US011351339B2

(12) United States Patent
Sarradon

(10) Patent No.: US 11,351,339 B2
(45) Date of Patent: Jun. 7, 2022

(54) ORIENTABLE CATHETER, DEVICE AND METHOD OF SURGICAL INTERVENTION

(71) Applicants: Pierre Sarradon, Le Castelet (FR); ARELFI HOLDING SPRL, Ucle (BE); DAVID CURIE INVEST, Dijon (FR)

(72) Inventor: Pierre Sarradon, Le Castelet (FR)

(73) Assignees: Pierre Sarradon, Le Castelet (FR); ARELFI HOLDING SPRL, Ucle (BE); DAVID CURIE INVEST, Dijon (FR)

( * ) Notice: Subject to any disclaimer, the term of this patent is extended or adjusted under 35 U.S.C. 154(b) by 46 days.

(21) Appl. No.: 16/616,070

(22) PCT Filed: May 22, 2018

(86) PCT No.: PCT/EP2018/063389
§ 371 (c)(1),
(2) Date: Nov. 22, 2019

(87) PCT Pub. No.: WO2018/215469
PCT Pub. Date: Nov. 29, 2018

(65) Prior Publication Data
US 2020/0086085 A1      Mar. 19, 2020

(30) Foreign Application Priority Data

May 22, 2017   (FR) ...................................... 1754531

(51) Int. Cl.
*A61M 25/01*      (2006.01)
*A61M 25/00*      (2006.01)

(52) U.S. Cl.
CPC ...... *A61M 25/0102* (2013.01); *A61M 25/007* (2013.01); *A61M 25/0041* (2013.01);
(Continued)

(58) Field of Classification Search
CPC .. A61M 2025/0004; A61M 2025/0175; A61M 2025/0681; A61M 25/0041;
(Continued)

(56) References Cited

U.S. PATENT DOCUMENTS 5,593,394 A * 1/1997 Kanesaka ......... A61M 25/0023
604/524
8,109,953 B1   2/2012 King, III et al.
(Continued)

FOREIGN PATENT DOCUMENTS

EP       0 827 756 A1    3/1998
WO    WO 02/11808 A2    2/2002

OTHER PUBLICATIONS

International Search Report and Written Opinion dated Jul. 30, 2018 in corresponding International Application No. PCT/EP2018/063389.

*Primary Examiner* — Deanna K Hall
(74) *Attorney, Agent, or Firm* — Chiesa Shahinian & Giantomasi

(57) ABSTRACT

An orientable catheter (10, 110, 210) comprising a first tubular body (16, 116, 216) having a distal portion with shape memory (26, 126, 226) which is curved at rest, and a second tubular body (38, 138, 238) having a distal stiffening portion (54, 154, 254) forming a stiffening element capable of sliding relative to the first tubular body (16, 116, 216) between a stiffening position in which the stiffening element (54, 154, 254) imposes a straightened configuration on the distal portion with shape memory (26, 126, 226), and a retracted position in which the stiffening element (54, 154, 254) does not interfere with the resting curved configuration of the distal end with shape memory (26, 126, 226).

17 Claims, 12 Drawing Sheets

(52) U.S. Cl.
CPC ............... *A61M 2025/0004* (2013.01); *A61M 2025/0175* (2013.01)

(58) Field of Classification Search
CPC ............ A61M 25/007; A61M 25/0102; A61M 25/0662; A61M 2025/0063; A61M 2025/0079
See application file for complete search history.

(56) References Cited

U.S. PATENT DOCUMENTS

| | | |
|---|---|---|
| 2009/0270835 A1 | 10/2009 | Kushner |
| 2010/0049171 A1 | 2/2010 | McQueen et al. |
| 2011/0152842 A1* | 6/2011 | Graffam ............ A61M 25/0102 604/540 |
| 2013/0018307 A1 | 1/2013 | Lee et al. |
| 2015/0283357 A1 | 10/2015 | Lampropoulos et al. |
| 2018/0056046 A1* | 3/2018 | Kiersey ................ A61F 2/2427 |

* cited by examiner

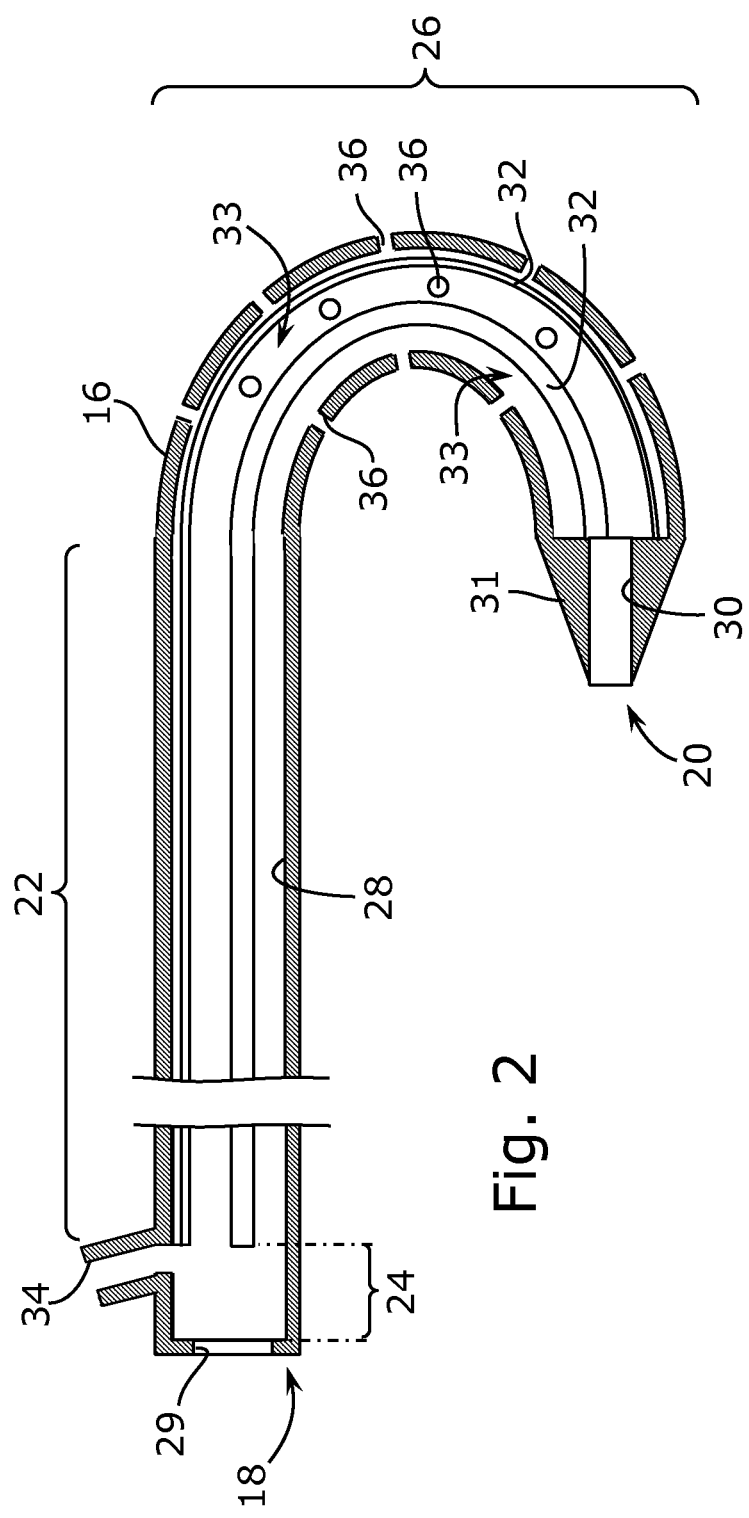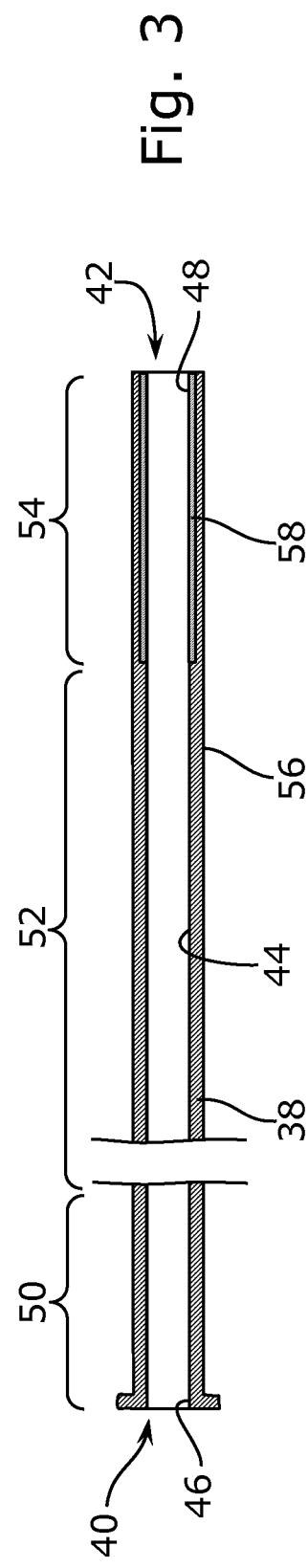

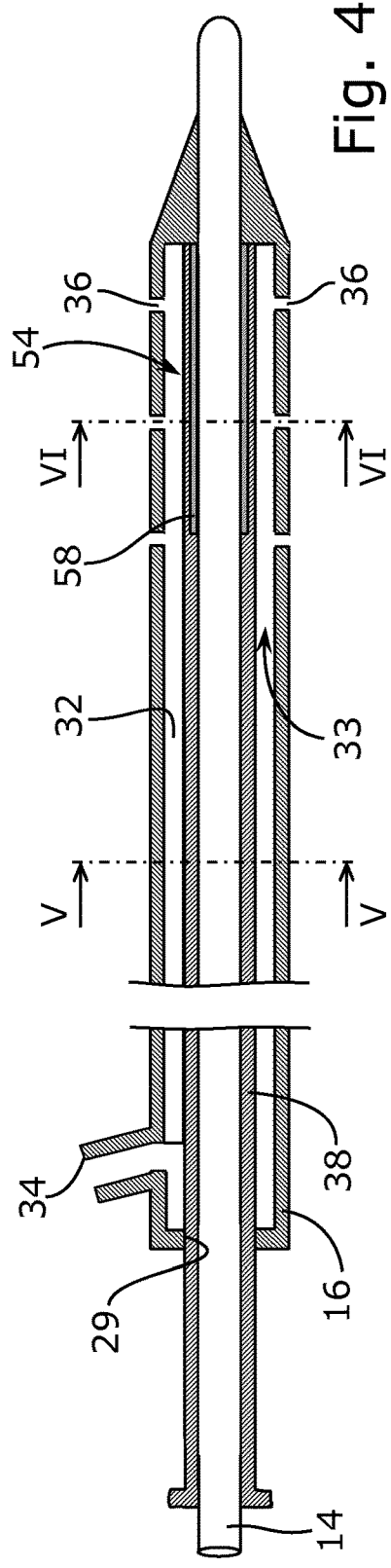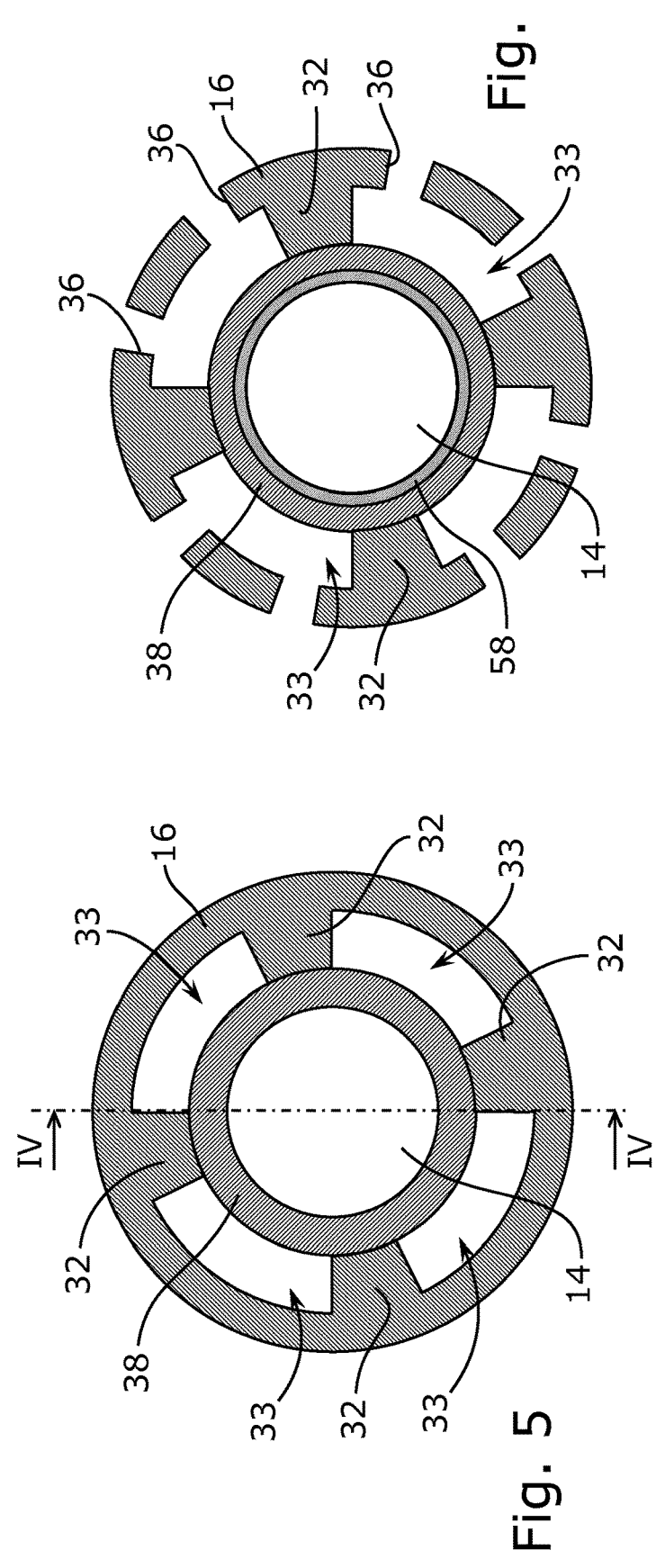

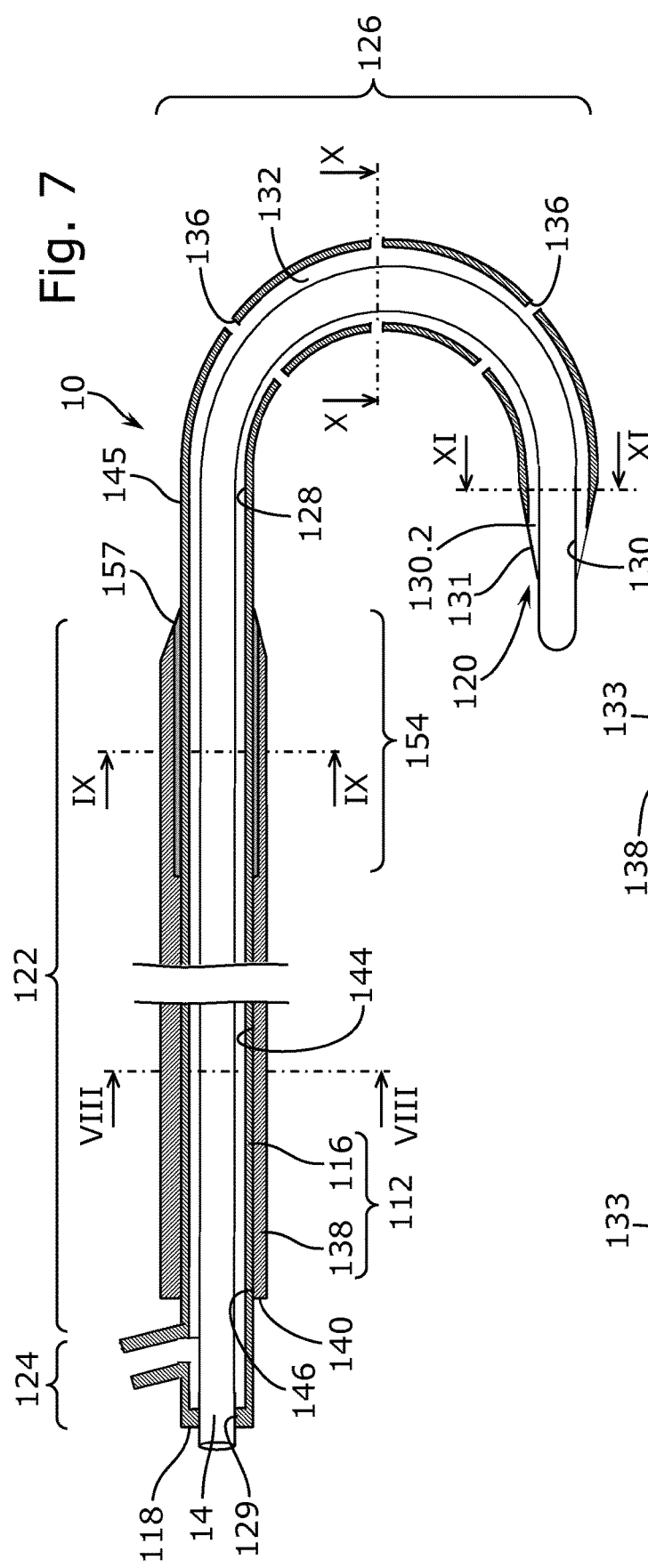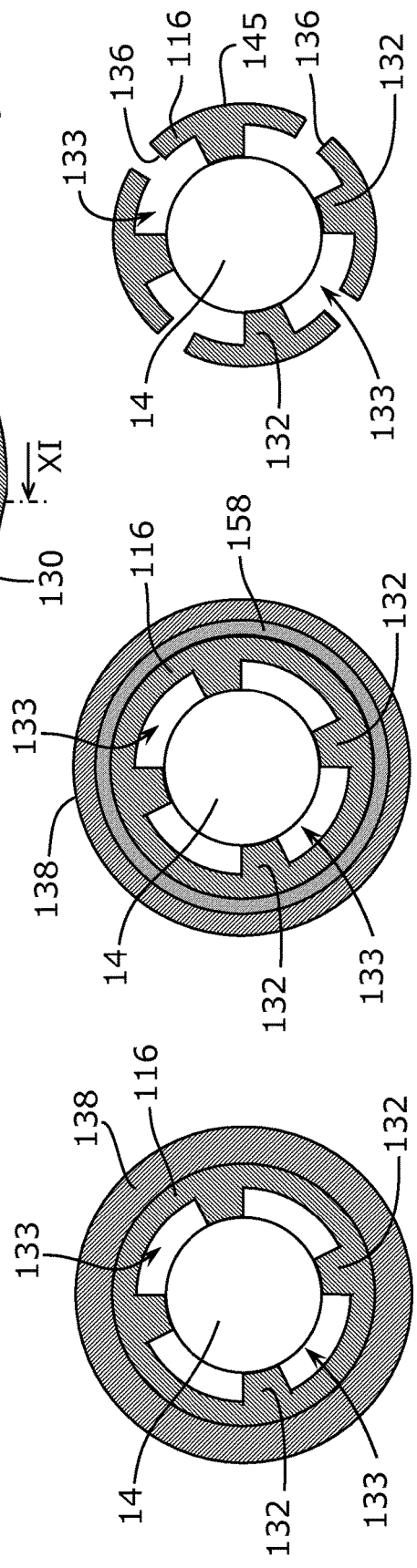

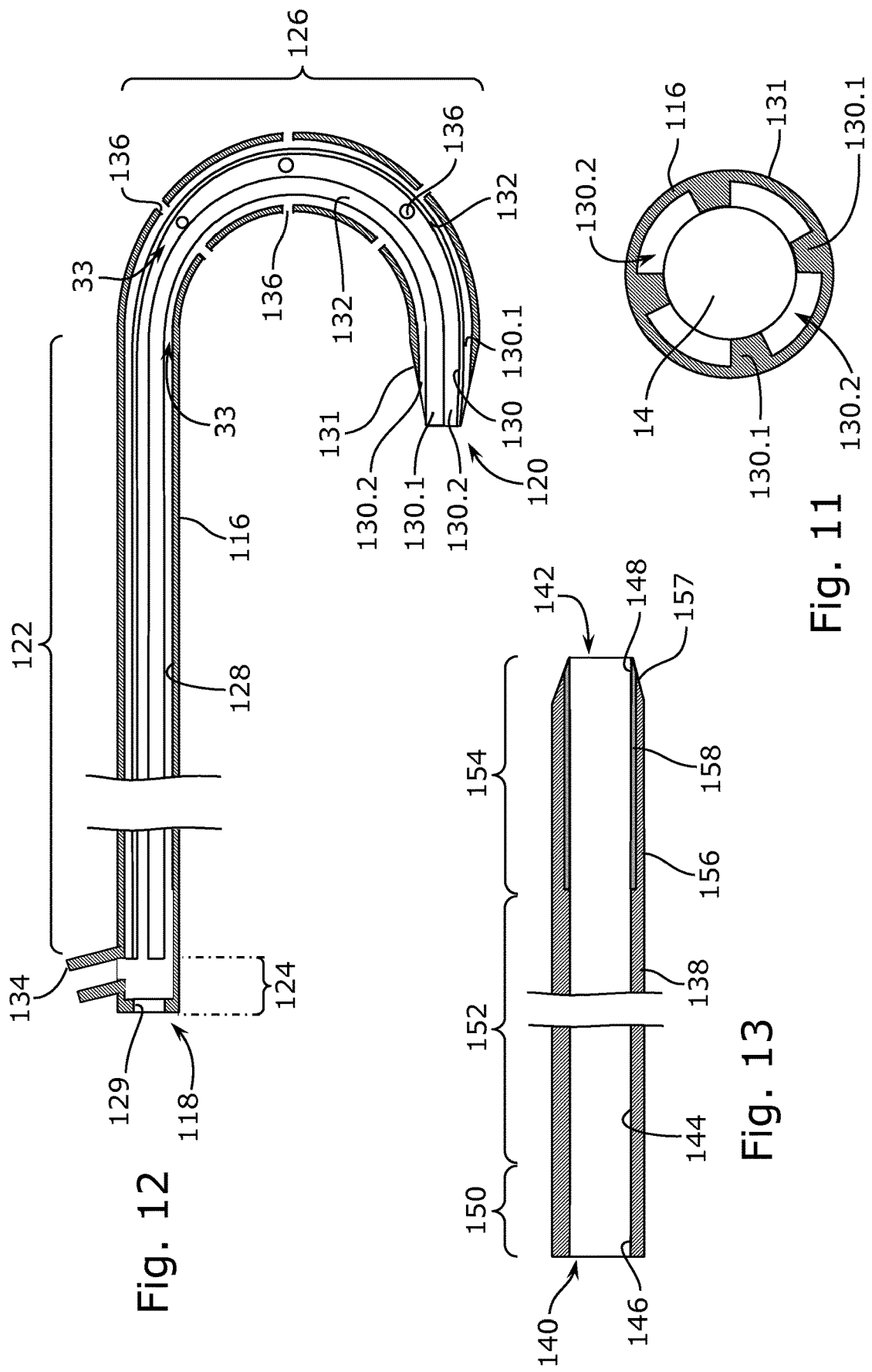

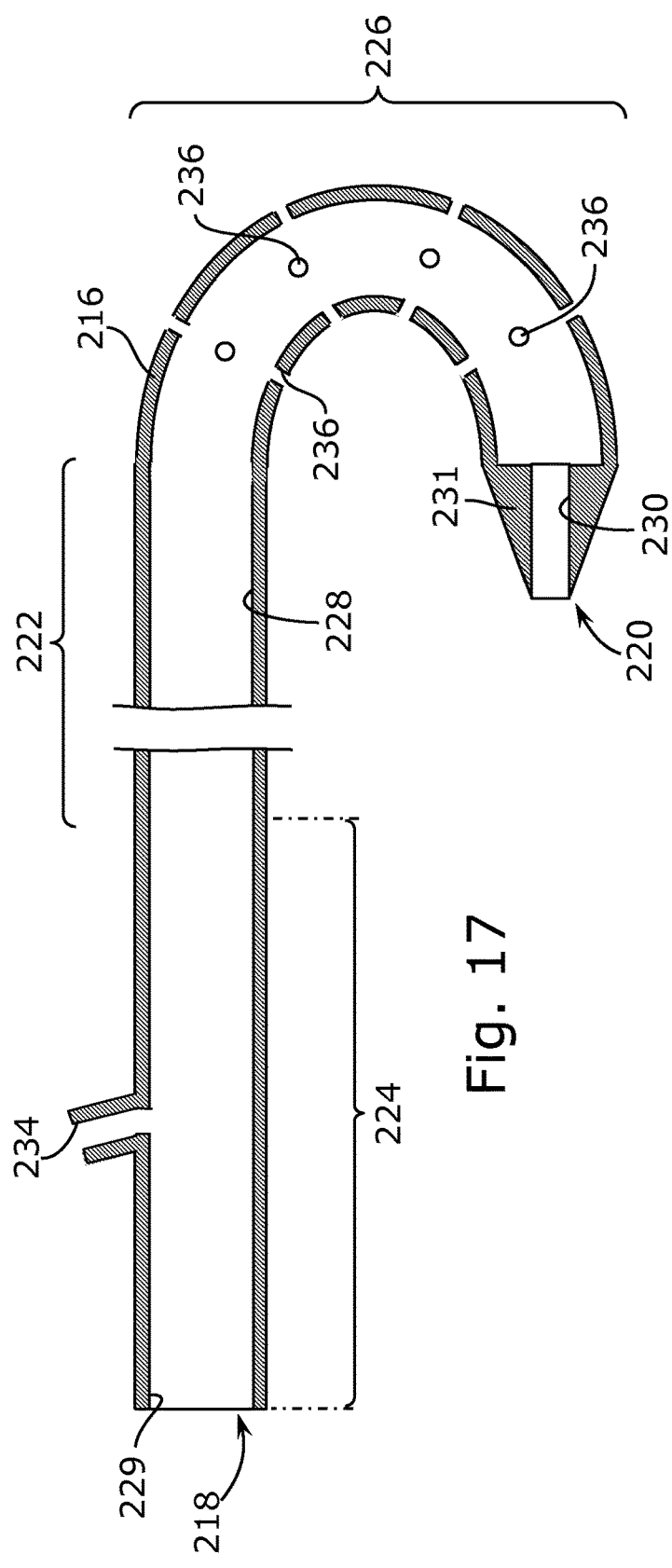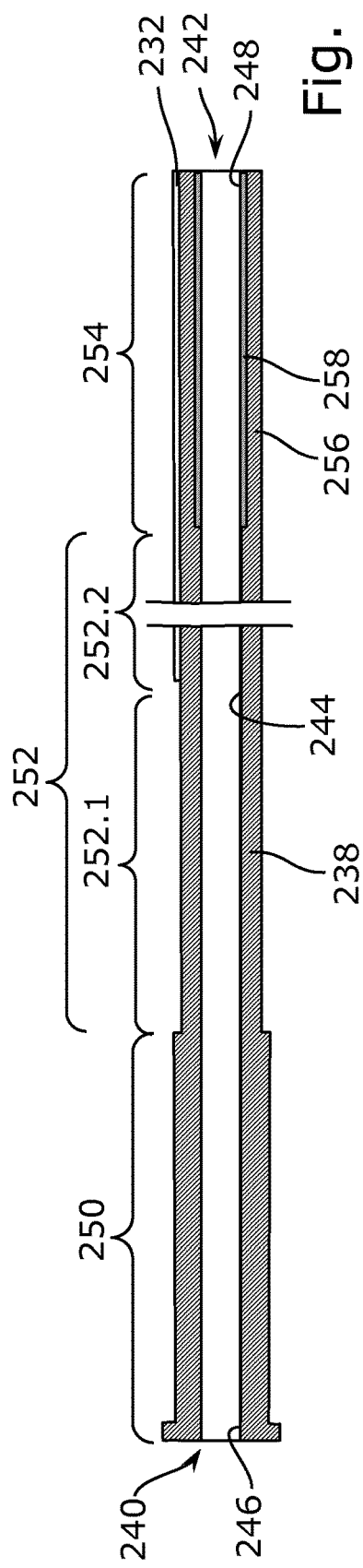

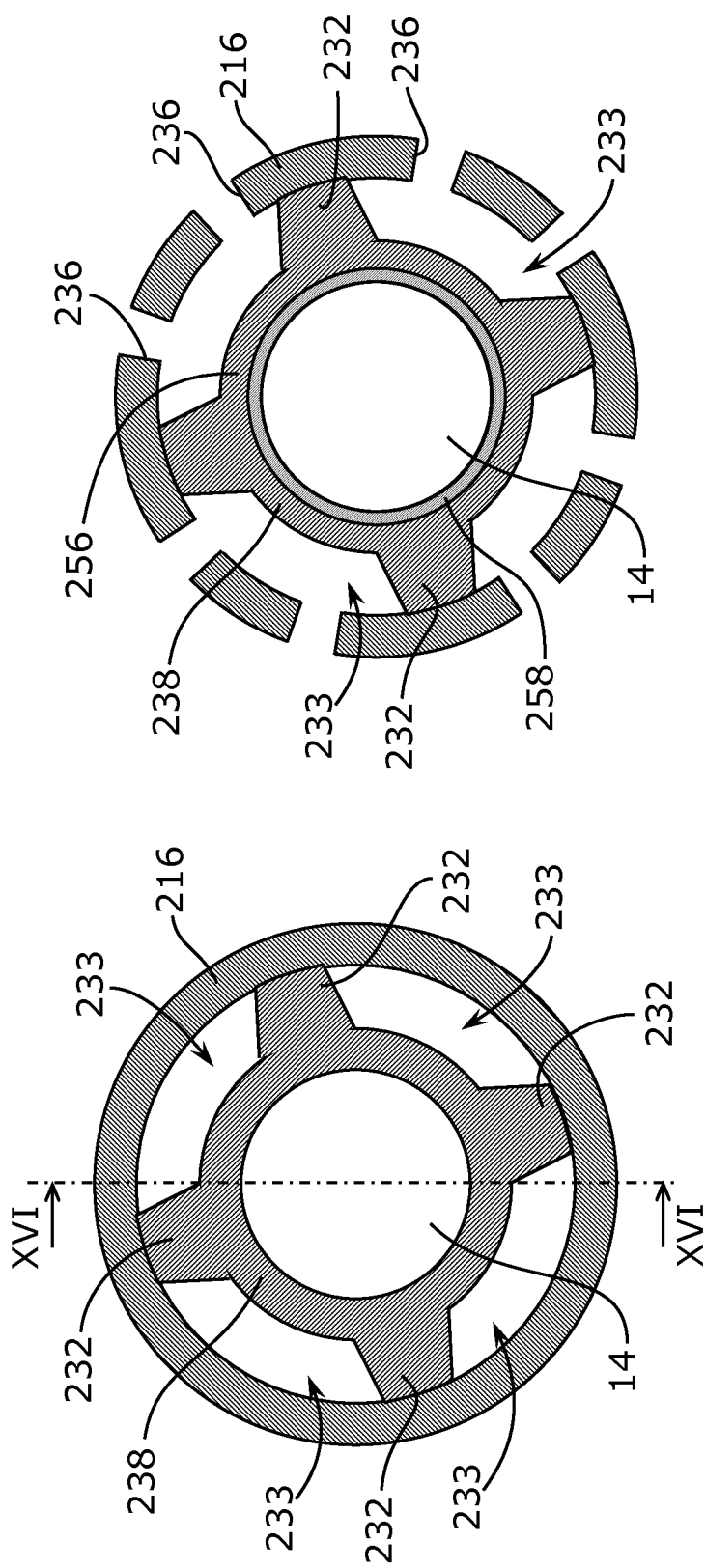

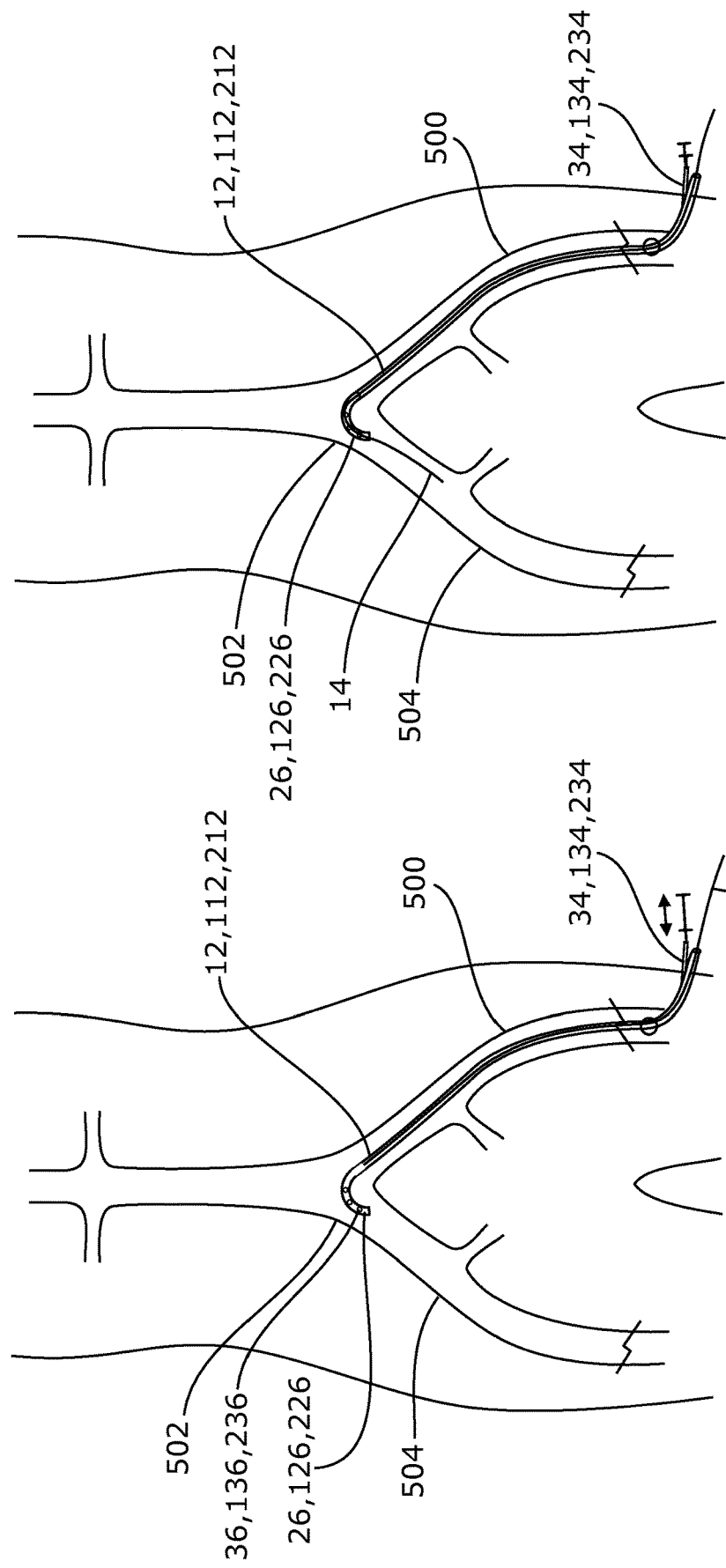

ORIENTABLE CATHETER, DEVICE AND METHOD OF SURGICAL INTERVENTION

CROSS-REFERENCE TO RELATED APPLICATIONS

This application is the National Stage entry under 35 U.S.C. § 371 of International Application No. PCT/EP2018/063389 filed on May 22, 2018, published on Nov. 29, 2018 under Publication Number WO 2018/215469 A1, which claims the benefit of priority under 35 U.S.C. § 119 of French Patent Application Number 1754531 filed on May 22, 2017, the entireties of which are herein incorporated by reference.

TECHNICAL FIELD OF THE INVENTION

The invention relates to an orientable catheter, a surgical device including this orientable catheter, and a method for surgery using this device.

PRIOR ART

Document US2013018307 describes an orientable catheter for paediatric cardiac surgery comprising a tubular body having a proximal end, a distal end, a flexible median portion, a distal portion with shape memory located between the flexible median portion and the distal end and having a curved configuration at rest, a first lumen opening at the proximal end and at the distal end, a second lumen opening at the proximal end, but closed at the distal end, and a stiffening cable housed in the second lumen and capable of sliding in the second longitudinal lumen between a stiffening position in which the stiffening cable is housed at least partially in the distal portion of the tubular body and imposes a straightened configuration on the distal portion with shape memory, and a retracted position in which the stiffening cable is housed outside the distal portion of the tubular body. This allows the distal end of the catheter to be guided while inserting a wire guide or medical device through the first lumen. However, the manufacture of a flexible multi-lumen tubular body with at least one lumen opening at both ends and one blind lumen is expensive and complex.

SUMMARY OF THE INVENTION

The invention aims to overcome the disadvantages of the prior art and to provide an orientable catheter whose structure is simplified and whose functions are preserved.

To do this, according to a first aspect of the invention, an orientable catheter is proposed comprising:
 a first tubular body having a longitudinal lumen and a distal portion with shape memory having a curved configuration at rest,
 a stiffening element capable of sliding relative to the first tubular body between a stiffening position in which the stiffening element imposes a straightened configuration on the distal portion with shape memory, and a retracted position in which the stiffening element does not interfere with the resting curved configuration of the distal end with shape memory, and
 a second tubular body having a longitudinal lumen and a distal stiffening portion forming the stiffening element, one of the first and second tubular bodies constituting an inner tubular body, the other of the first and second tubular bodies constituting an outer tubular body, the inner tubular body sliding inside the longitudinal lumen of the outer tubular body so as to slide the stiffening element between the stiffening position and the retracted position.

The longitudinal lumen of the inner tubular body can thus be used to pass and guide a wire guide, or to inject a product such as a contrast agent or a drug. The coaxial structure between the outer tubular body and the inner tubular body is particularly simple.

Preferably, the distal portion with shape memory of the first tubular body has an end portion comprising a distal end of the first tubular body and having a cross-section that gradually increases from the distal end of the first tubular body away from the distal end of the first tubular body. The distal end is thus profiled to facilitate its passage through the blood vessels. In longitudinal section, this profile can be rounded or partially rounded and partially frustoconical.

Preferably, the outer tubular body has a cylindrical outer wall with a circular base, the distal portion of the outer tubular body preferably has an end portion including a distal end of the outer tubular body and having a cross-section that gradually increases from the distal end of the outer tubular body away from the distal end of the outer tubular body until the cylindrical outer wall. In longitudinal section, the profile of the end portion can be rounded or partially rounded and partially frustoconical. The circular outer section of the outer tubular body facilitates its passage through the blood vessels.

In practice, the first tubular body has a proximal end, a distal end, a longitudinal lumen opening through a proximal port onto the proximal end of the first tubular body and through a distal port onto the distal end of the first tubular body, a proximal portion including the proximal end of the first tubular body, a flexible median portion, the distal portion with shape memory being located between the flexible median portion of the first tubular body and the distal end of the first tubular body.

According to a particularly advantageous embodiment, the distal portion with shape memory of the first tubular body is provided with one or more distal side ports opening into the longitudinal lumen of the first tubular body, the orientable catheter having one or more communication channels connecting the proximal portion of the first tubular body with the one or more distal side ports at least when the stiffening element is in the retracted position. The one or more distal side ports allow an injection of liquid product, for example a drug or contrast agent, when the longitudinal lumen inside the inner tubular body is occupied by a wire guide. Preferably, the one or more communication channels together have an area of more than 0.15 mm² in cross-section when the stiffening element is in the retracted position.

Rather than providing an additional specific lumen to form the one or more channels, it would be better to form the communication channels in the longitudinal lumens of the inner and/or outer tubular body. According to one embodiment, the communication channels are delimited at least partially by a wall of the longitudinal lumen of the first tubular body, when the stiffening element is in the retracted position.

It is essential for the one or more communication channels to allow communication when the stiffening element is retracted, to allow radiological visualization in this position. According to one structurally simple embodiment, the one or more communication channels do not connect the proximal portion of the first tubular body with the distal side ports when the stiffening element is in the stiffening position. According to one alternative embodiment, the one or more communication channels connect the proximal portion of the first tubular body with the distal side ports when the stiffening element is in the stiffening position. It is then also possible to inject in the stiffening position, which provides a more complete visualization function.

Preferably, the proximal portion of the first tubular body is provided with a lateral or axial access connection, communicating with the one or more communication channels. This connection must allow a liquid to be injected using a syringe.

According to one embodiment, the first tubular body is the outer tubular body.

According to an alternative embodiment, the first tubular body is the inner tubular body. In this hypothesis, it would be advisable to provide for the distal portion of the second tubular body to comprise an end portion comprising the distal end of the second tubular body and having a section that gradually increases from the distal end of the second tubular body towards the median portion of the second tubular body.

In practice, the second tubular body has a proximal end, a distal end, a longitudinal lumen opening through a proximal port onto the proximal end of the second tubular body and through a distal port onto the distal end of the second tubular body, a proximal portion including the proximal end of the second tubular body, a flexible median portion constituting the flexible link, the distal stiffening portion being located between the flexible median portion of the second tubular body and the distal end of the second tubular body. The middle section of the second tubular body is a connection between the stiffening element and the proximal end of the second tubular body, which is used during the operation to slide the second tubular body relative to the first tubular body.

Another aspect of the invention relates to a surgical device, which includes an orientable catheter as described above, and a flexible wire guide that can be inserted into the longitudinal lumen of the inner tubular body and exit through the distal port of the first tubular body. In practice, the wire guide will be cylindrical with a circular periphery in cross-section and a profiled distal end, preferably rounded so as to facilitate its passage through the blood vessels without damaging same.

Preferably, the distal port of the first tubular body is cylindrical and matches the cross-section of the wire guide, so that the wire guide is able to slide into the distal port of the first tubular body while sealing the distal port of the first tubular body. This sealing will be particularly advantageous when the catheter is provided with one or more communication channels connecting the proximal portion of the first tubular body with one or more distal side ports and the one or more communication channels are formed at least partially in the longitudinal lumen of the inner tubular body. Indeed, in such a case, the seal ensures that the injected liquid will be discharged laterally through the distal side ports, rather than axially through the distal end port.

Another aspect of the invention relates to a method for surgery using a surgical device as described above, the method comprising the following consecutive steps:
  the wire guide is inserted into a first blood vessel, until a junction of a second blood vessel;
  the orientable catheter is inserted into the first blood vessel, the stiffening element being in the stiffening position, by causing the wire guide held stationary to penetrate the longitudinal lumen of the inner tubular body;
  the stiffening element is retracted into the retracted position, releasing the distal portion with shape memory, which expands and penetrates the junction of the second blood vessel; and then
  the wire guide is pushed back into the longitudinal lumen of the inner tubular body so that the wire guide opens into the distal end of the first tubular body and progresses into the second blood vessel.

Preferably, a step of injecting a contrast agent into the one or more communication channels is provided when the stiffening element is in the stiffening position. This step involves identifying the correct position of the catheter in relation to the junction of the second blood vessel before retracting the rigidification element into the retracted position. The contrast agent may, in particular, be ejected through one or more distal side ports of the first tubular body and/or through a distal end port of the inner tubular body.

Preferably, a step is provided of injecting a contrast agent into the one or more communication channels when the stiffening element is in the retracted position. This step involves checking the correct relaxation and penetration of the distal portion with shape memory of the catheter into the junction of the second blood vessel. The contrast agent may, in particular, be ejected through one or more distal side ports of the first tubular body and/or through a distal end port of the inner tubular body.

Preferably, the method also includes the following subsequent steps:
  the stiffening element is slid into the stiffening position by holding the wire guide and the middle section of the first tubular body stationary;
  the orientable catheter is slid over the wire guide to move the distal portion of the second tubular body into the second blood vessel.

The method is particularly suitable for an operation in which the first blood vessel is the femoral artery and the second blood vessel is the common iliac artery.

According to a first variant of the method, the retraction of the wire guide is complete and followed by an injection of a contrast agent into the longitudinal lumen of the inner tubular body until the junction of the second vessel.

According to another variant of the method, a contrast agent is injected into the one or more passages, after at least partially retracting the wire guide or after retracting the stiffening element into the retracted position, releasing the distal portion with shape memory, which expands and penetrates the junction of the second blood vessel.

Preferably, the contrast agent is distributed in the junction of the second vessel at least partially through the side ejection ports.

According to another aspect of the invention, it relates to an orientable catheter comprising:
  a first tubular body having a proximal end, a distal end, a longitudinal lumen opening through a proximal port onto the proximal end of the first tubular body and through a distal port onto the distal end of the first tubular body, a proximal portion including the proximal end of the first tubular body, a flexible median portion, and a distal portion with shape memory located between the flexible median portion of the first tubular body and the distal end of the first tubular body, the distal portion with shape memory having a curved configuration at rest, the distal portion with shape memory being provided with one or more distal side ports opening into the longitudinal lumen of the first tubular body, a second tubular body having a longitudinal lumen and a distal stiffening portion forming a stiffening element capable of sliding relative to the first tubular body between a stiffening position in which the stiffening element imposes a straightened configuration on the distal portion with shape memory, and a retracted position in which the stiffening element does not interfere with the resting curved configuration of the distal end with shape memory, According to this aspect of the invention, one of the first and second tubular bodies constitutes an inner tubular body, and the other of the first and second tubular bodies constitutes an outer tubular body, the inner tubular body sliding inside the longitudinal lumen of the outer tubular body in order to slide the stiffening element between the stiffening position and the retracted position. The orientable catheter has one or more communication channels connecting the proximal portion of the first tubular body with the distal side ports when the stiffening element is in the retracted position and connecting the proximal portion of the first tubular body with the distal side ports or with the distal port at the distal end of the first tubular body when the stiffening element is in the stiffening position.

BRIEF DESCRIPTION OF THE FIGURES

Further characteristics and advantages of the invention will be clear from reading the following description, made in reference to the appended figures, which show:

FIG. 2, a schematic axial cross-sectional view of a first tubular body of the surgical device of FIG. 1;

FIG. 3, a schematic axial cross-sectional view of a second tubular body of the surgical device of FIG. 1;

FIG. 4, a schematic axial cross-sectional view of the surgical device of FIG. 1, in rectilinear position, in section plane IV-IV of FIG. 5;

FIG. 5, a schematic cross-sectional view of the surgical device of FIG. 1 in section plane V-V of FIG. 4;

FIG. 6, a schematic cross-sectional view of the surgical device of FIG. 1 in section plane VI-VI of FIG. 4;

FIG. 7, a schematic axial cross-sectional view of a surgical device according to a second embodiment of the invention, in a rest position;

FIG. 8, a schematic cross-sectional view of the surgical device of FIG. 7 in section plane VIII-VIII of FIG. 7;

FIG. 9, a schematic cross-sectional view of the surgical device of FIG. 7 in section plane IX-IX of FIG. 7;

FIG. 10, a schematic cross-sectional view of the surgical device of FIG. 7 in section plane X-X of FIG. 7;

FIG. 11, a schematic cross-sectional view of the surgical device of FIG. 7 in section plane XI-XI of FIG. 7;

FIG. 12, a schematic axial cross-sectional view of a first tubular body of the surgical device of FIG. 7;

FIG. 13, a schematic axial cross-sectional view of a second tubular body of the surgical device of FIG. 7;

FIG. 17, a schematic axial cross-sectional view of a first tubular body of the surgical device of FIG. 15;

FIG. 18, a schematic axial cross-sectional view of a second tubular body of the surgical device of FIG. 15;

FIG. 19, a schematic cross-sectional view of the surgical device of FIG. 1 in section plane XIX-XIX of FIG. 16;

FIG. 20, a schematic cross-sectional view of the surgical device of FIG. 1 in section plane XX-XX of FIG. 16;

FIG. 23, a schematic view of a third step of a surgical operation using the surgical device according to the invention;

FIG. 24, a schematic view of a fourth step of a surgical operation using the surgical device according to the invention;

Figure 1:
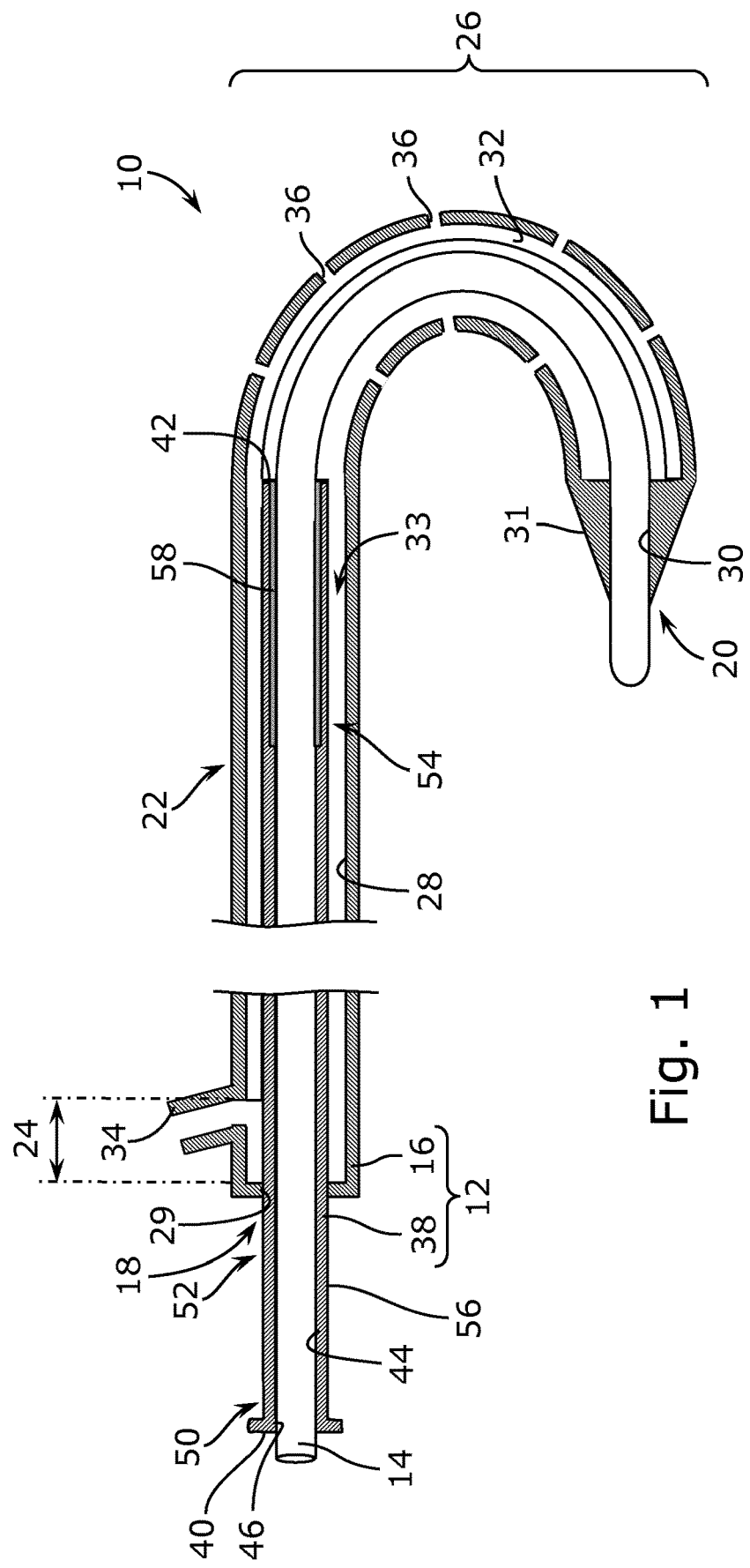
FIG. 1, a schematic axial cross-sectional view of a surgical device according to a first embodiment of the invention, in a rest position.
Figure 14:
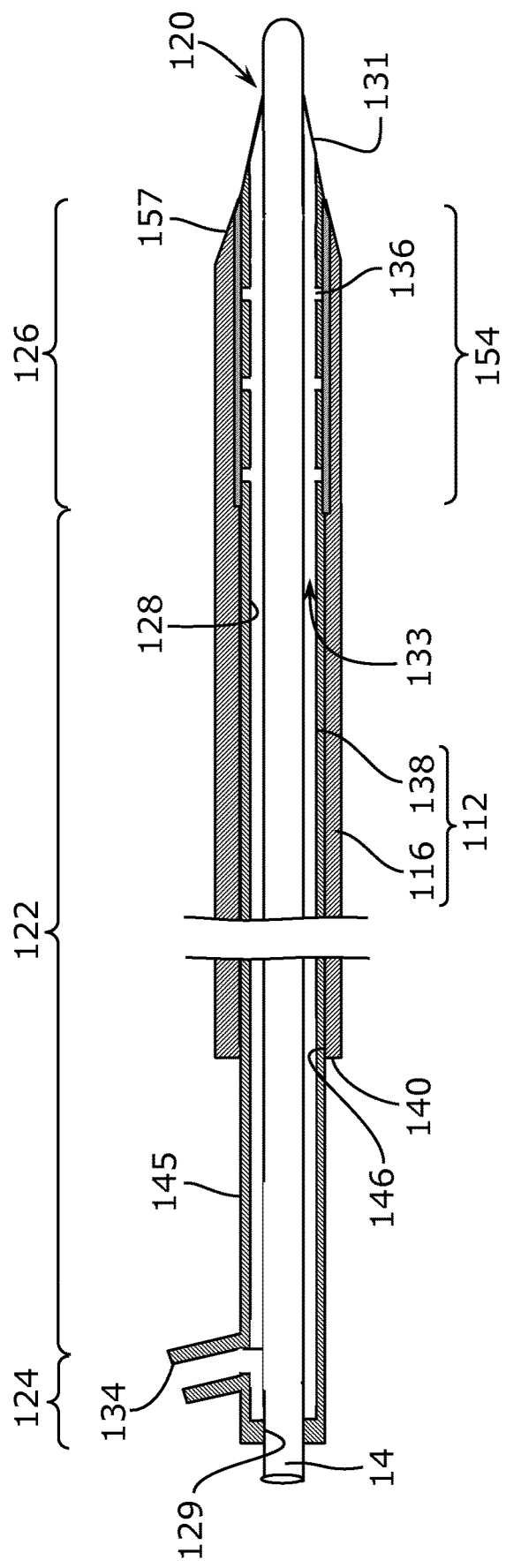
FIG. 14, a schematic axial cross-sectional view of the surgical device of FIG. 7, in straightened position.

For greater clarity, identical or similar features are identified by identical reference signs in all the figures.

DETAILED DESCRIPTION OF EMBODIMENTS

FIGS. 1 to 6 show a surgical device 10 according to a first embodiment of the invention, comprising an orientable catheter 12 and a flexible wire guide 14. The orientable catheter 12 has a first outer tubular body 16, shown in detail in FIG. 2, having a proximal end 18, a distal end 20, a flexible median portion 22, a proximal portion 24 located between the flexible median portion 22 and the proximal end 18, and a distal portion with shape memory 26 located between the flexible median portion 22 and the distal end 20. A longitudinal lumen 28 is formed in the outer tubular body 16, this longitudinal lumen 28 opening through a proximal port 29 onto the proximal end 18 of the outer tubular body 16 and through a distal port 30 onto the distal end 20 of the outer tubular body 16. The distal portion 26 has an end portion 31 whose cross-section decreases as it approaches the distal end 20. The distal port 30 is designed to allow the wire guide 14 to slide snugly through the distal port 30, while maintaining a good seal at this interface. The wall of the longitudinal lumen 28 of the outer tubular body 16 has longitudinal ribs 32 defining longitudinal communication channels 33 therebetween, extending at least over the entire length of the median portion 22 and the distal portion 26 of the outer tubular body 16. The ribs 32 are interrupted in the proximal portion 24. The proximal portion 24 of the outer tubular body 16 is provided with a proximal side connection port 34 opening into a portion of the longitudinal lumen 28 without ribs. The distal portion 26 of the outer tubular body 16 has side ejection ports 36 opening into the communication channels 33.

Remarkably, the distal portion with shape memory 26 has a curved configuration at rest, as shown in FIGS. 1 and 2. Distal portion with shape memory is understood to mean a deformable distal portion, at least between a curved rest position, preferably forming an angle at rest greater than 90° or even greater than 120° or, as shown in FIGS. 1 and 2, an angle at rest of 180° or more, and a straight position shown in FIG. 4, and preferably capable of adopting all intermediate positions between the curved rest position and the straight position.

The orientable catheter 12 also comprises a second inner tubular body 38 housed in the longitudinal lumen 28 of the outer tubular body 16 and capable of sliding in the longitudinal lumen 28. The inner tubular body 38, shown in detail in FIG. 3, has a proximal end 40, a distal end 42, and a longitudinal lumen 44 aligned with the longitudinal lumen 28, opening through a proximal port 46 onto the proximal end 40 of the inner tubular body 38 and through a distal port 48 onto the distal end 42 of the inner tubular body 38. The longitudinal lumen 44 preferably has a circular cross-section, and its inner diameter is suited to the sliding of the wire guide 14, which is itself cylindrical with a circular base. The inner tubular body 38 has a proximal portion 50 including the proximal end 40, a flexible median portion 52 and a rigid rectilinear distal portion 54 located between the flexible proximal portion 52 and the distal end 42. The outer wall 56 of the inner tubular body 38 is cylindrical with a circular base. The rigid distal portion 54 can be produced by any appropriate means, here by a rigid insert 58 overmoulded with an outer sheath made of the material that constitutes the proximal 50 and median 52 portions. The proximal port 29 is cylindrical with a circular base and a cross-section matching that of the outer wall 56, so as to allow the inner tubular body 38 to slide snugly through the proximal port 29 while maintaining liquid tightness at this interface.

Once the inner tubular body 38 is inserted into the lumen 28 of the outer tubular body 16, the ribs 32 bear against the outer wall 56 of the inner tubular body 38, as shown in FIGS. 5 and 6. The ribs 32 have a guiding function that allows the inner tubular body 38 to slide into the outer tubular body.

The rigid distal portion 54 of the inner tubular body 38 constitutes a stiffening element housed in the longitudinal lumen 28 and capable of sliding in the longitudinal lumen 28 between a retracted position shown in FIG. 1 and a stiffening position shown in FIG. 4. In the stiffening position of FIG. 4, the stiffening element 54 is housed in the distal portion with shape memory 26 of the outer tubular body 16 and imposes a straightened configuration on the distal portion with shape memory 26. In the retracted position, on the other hand, the stiffening element 54 is housed outside the distal portion with shape memory 26 of the outer tubular body 16, allowing it to return to its curved rest position, as shown in FIG. 1. There are naturally an infinite number of positions between these two extreme positions: it is thus possible, by adjusting the relative position of the rigid distal portion 54 of the inner tubular body 38 and the distal portion with shape memory 26 of the outer tubular body 16, to continuously vary the orientation of the distal portion with shape memory 26 between its rest position and the straight position. It should be noted here that in this application, the term "rigid" used to refer to the rigid rectilinear distal portion 54 refers to the ability of the rigid rectilinear distal portion 54 to impose its shape on the distal portion with shape memory 26. However, the rigid rectilinear distal portion 54 remains flexible enough to follow the path imposed by the wire guide 14 as it passes through the blood vessels.

The flexible proximal portion 50 of the inner tubular body 38 constitutes a link between the stiffening element 54 and the proximal end 40 of the inner tubular body 38, which always projects from the proximal end 18 of the outer tubular body 16. Communication channels 33 are intended to provide one or more pathways from the proximal connection 34 to the distal side ports 36, between the inner tubular body 38 and the outer tubular body 16, in particular for injecting a liquid, for example a contrast agent or a drug. The absence of ribs 32 in the proximal portion 24 of the outer tubular body 16 allows a good distribution of the liquid between the communication channels 33. The sealed interface between the inner tubular body 38 and the proximal port 29 and between the wire guide 14 and the distal port 30 also ensures that the liquid injected by the proximal connection 34 is ejected mainly through at least the distal side ports 36. The pathways are formed both when the inner tubular body 38 is in the stiffening position, as shown in FIGS. 4 to 6, and when the inner tubular body 38 is retracted in the position shown in FIG. 1. In this position, the individualized channels 33 are extended by a common section consisting of the lumen 28 in the distal portion 26 of the outer tubular body 16. The cumulative flow area of the communication channels 33 must be sufficient to allow the passage of a viscous fluid such as a contrast liquid, and preferably has a surface area greater than 0.15 mm$^2$.

FIGS. 7 to 14 show a surgical device 110 according to a second embodiment of the invention, comprising an orientable catheter 112 and a flexible wire guide 14. The 112 orientable catheter has a first inner tubular body 116, having a proximal end 118, a distal end 120, a flexible median portion 122, a proximal portion 124 located between the flexible median portion 122 and the proximal end 118, and a distal portion with shape memory 126 located between the flexible median portion 122 and the distal end 120. A longitudinal lumen 128 is formed in the inner tubular body 116, this longitudinal lumen 128 opening through a proximal port 129 onto the proximal end 118 of the inner tubular body 116 and through a distal port 130 onto the distal end 120 of the inner tubular body 116. The proximal port 129 is cylindrical with a circular base and a cross-section matching that of the wire guide 14, so as to allow the inner tubular body 116 to slide snugly over the wire guide 14 while maintaining liquid tightness at this interface. The distal portion 126 has an end portion 131 whose cross-section decreases as it approaches the distal end 120. The distal port 130 has longitudinal ribs 130.1 to allow the wire guide 14 to slide snugly, while preserving one or more distal ejection channels 130.2 between the longitudinal lumen 128 and the outside. The wall of the longitudinal lumen 128 of the inner tubular body 116 has longitudinal ribs 132 defining longitudinal communication channels 133 therebetween, extending at least over the entire length of the median portion 122 and the distal portion 126 of the inner tubular body 116. The ribs 132 are interrupted in the proximal portion 124. The proximal portion 124 of the inner tubular body 116 is provided with a proximal side connection port 134 opening into the portion of the longitudinal lumen 128 without ribs. The distal portion 126 of the inner tubular body 116 has side ejection ports 136 opening into the communication channels 132. Remarkably, the distal portion with shape memory 126 has a curved configuration at rest, as shown in FIGS. 7 and 12. Once the wire guide 14 is inserted into the lumen 128 of the inner tubular body 116, the ribs 132 bear against the cylindrical outer wall of the wire guide 14. The ribs 132 have a guiding function that allows the wire guide 14 to slide into the inner tubular body 116.

The orientable catheter 112 also comprises a second outer tubular body 138 in which the inner tubular body 116 slides. The outer tubular body 138, shown in detail in FIG. 13, has a proximal end 140, a distal end 142, and a longitudinal lumen 144 aligned with the longitudinal lumen 128, opening through a proximal port 146 onto the proximal end 140 of the outer tubular body 138 and through a distal port 148 onto the distal end 142 of the outer tubular body 138. The longitudinal lumen 144 preferably has a circular cross-section, and its inner diameter is suited to the sliding of the inner tubular body 116, whose outer wall 145 is cylindrical with a circular base. The outer tubular body 138 has a proximal portion 150 including the proximal end 140, a flexible median portion 152 and a rigid rectilinear distal portion 154 located between the flexible proximal portion 152 and the distal end 142. The outer wall 156 of the outer tubular body 138 is cylindrical with a circular base. The rigid distal portion 154 can be produced by any appropriate means, here by an insert 158 overmoulded with the material that constitutes the proximal 150 and median 152 portions and the outer wall at the distal portion 154. The distal portion 156 has an end portion 157 whose cross-section decreases as it approaches the distal end 142.

The rigid distal portion 154 of the outer tubular body 138 constitutes a stiffening element capable of sliding on the inner tubular body 116 between a retracted position shown in FIGS. 7 to 10 and a stiffening position shown in FIG. 13. In the stiffening position, the stiffening element 154 at least partially covers the distal portion with shape memory 126 of the inner tubular body 116 and imposes a straightened configuration on the distal shape memory 126 portion as shown in FIG. 13. In the retracted position, on the other hand, the stiffening element 154 does not cover the distal portion with shape memory 126 of the inner tubular body 116, allowing it to return to its curved rest position. The flexible proximal portion 150 of the outer tubular body 138 constitutes a link between the stiffening element 154 and the proximal end 140 of the outer tubular body 138.

The communication channels 133 are intended to provide one or more pathways from the proximal connection 134 to the distal side ports 136, between the inner tubular body 138 and the wire guide 14 for an injected liquid, for example a contrast liquid or a drug. The absence of ribs 132 in the proximal portion 124 of the inner tubular body 116 allows a good distribution of the liquid between the communication channels 133. The sealed interface between the wire guide 14 and the proximal port 129 also ensures that the liquid injected by the proximal connection 134 is ejected towards the distal end of the inner tubular body 138, to the distal side ports 136 and the distal ejection channels 130.2.

It should be noted that in the stiffening position, it is not provided for liquid to be distributed through the distal side ports 136, which are covered by the stiffening element 154. In this position, the product is ejected axially through the distal port 130 via distal ejection channels 130.2, without the need to retract the wire guide 14. However, in an alternative embodiment, one or more distal side ports may be provided in the rigid distal portion 154 of the outer tubular body 138, positioned in such a way that in the stiffening position, these distal side ports are aligned with the distal side ports 136, or in communication with same through channels formed between the outer tubular body 138 and the inner tubular body 116. In this case, it is possible to distribute a liquid through the distal side ports 136, and the distal side ports of the rigid distal portion 154 of the outer tubular body 138 in the stiffening position.

FIGS. 15 to 20 show a surgical device 210 comprising an orientable catheter 212 and a flexible wire guide 14. The orientable catheter 12 differs from the embodiment of FIGS. 1 to 6 essentially in the positioning of the guide ribs 232, which have the same function as the guide ribs 32 but are positioned on the outer wall 256 of the inner tubular body 138. Thus, the guide ribs 232 do not only have the function of delimiting the channels of the longitudinal communication channels 33, and of guiding between the first tubular body 216 and the second tubular body 238, but also contribute to the stiffening of the second tubular body 238. The guide ribs 232 extend at least in the distal portion 254 of the inner tubular body 238. If necessary, the intermediate portion 252 of the inner tubular body 238 can be subdivided into a portion 238.1 without guide ribs 232, close to the proximal portion 250, and a portion 238.2 with guide ribs 232, close to the distal portion 254.

To ensure sealing at the proximal port 229 of the outer tubular body 216, the proximal portion 250 of the inner tubular body 238 is extended, and has an outer diameter equal to the outer diameter at the ribs 232 and the inner diameter of the longitudinal lumen 228 formed in the outer tubular body 216. The longitudinal lumen 228 is cylindrical with a circular base and smooth. In addition, the length of the proximal portion 224 of the outer tubular body 216 is adapted so that in the retracted position in FIG. 15 as well as in the stiffening position in FIG. 16, the proximal side connection port 234 opens between the proximal portion 250 and the ribbed portion 232 of the inner tubular body 238. In the distal portion 226, the outer tubular body 216 is provided with side ejection ports 236.

In their other components and in their operation, the orientable catheter 212 and the surgical device 210 are essentially similar to the orientable catheter 12 and the surgical device 10 of the first embodiment. For the sake of simplicity, the identical components have been referenced of FIGS. 15 to 20 by numbers derived from the numbers used of FIGS. 1 to 6, increasing them by 200.

Figure 15:
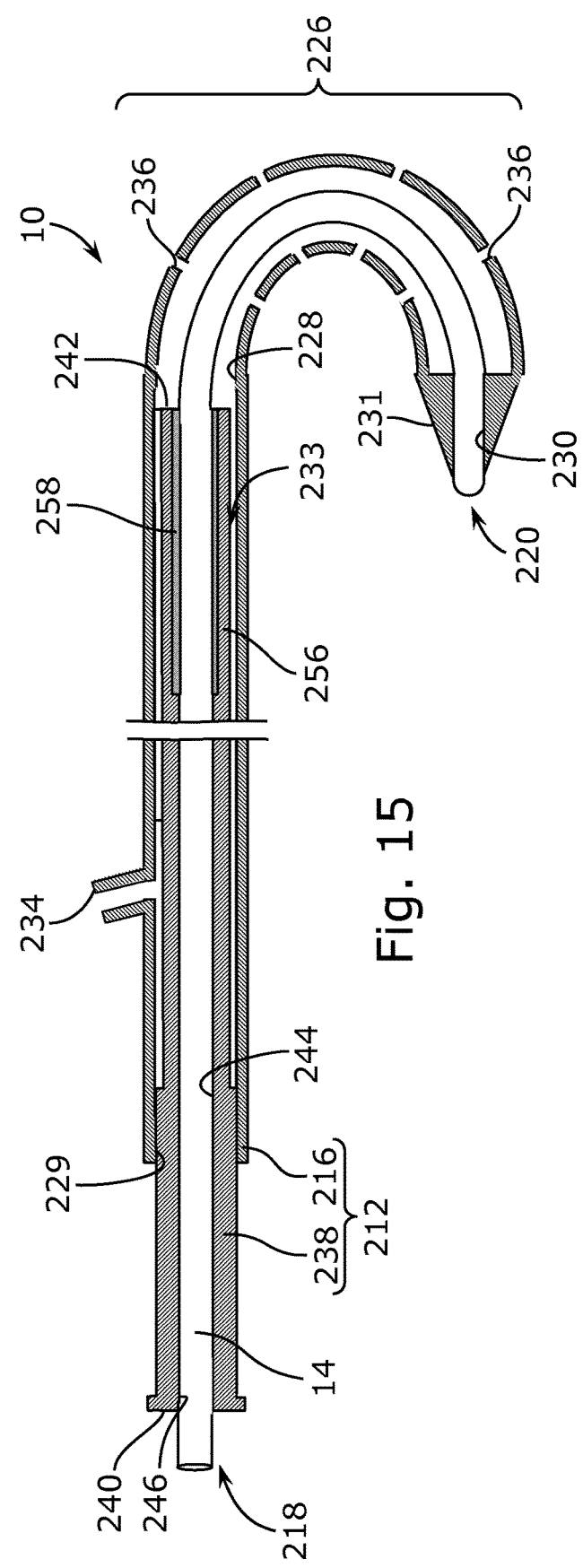
FIG. 15, a schematic axial cross-sectional view of a surgical device according to a third embodiment of the invention, in a rest position.
Figure 16:
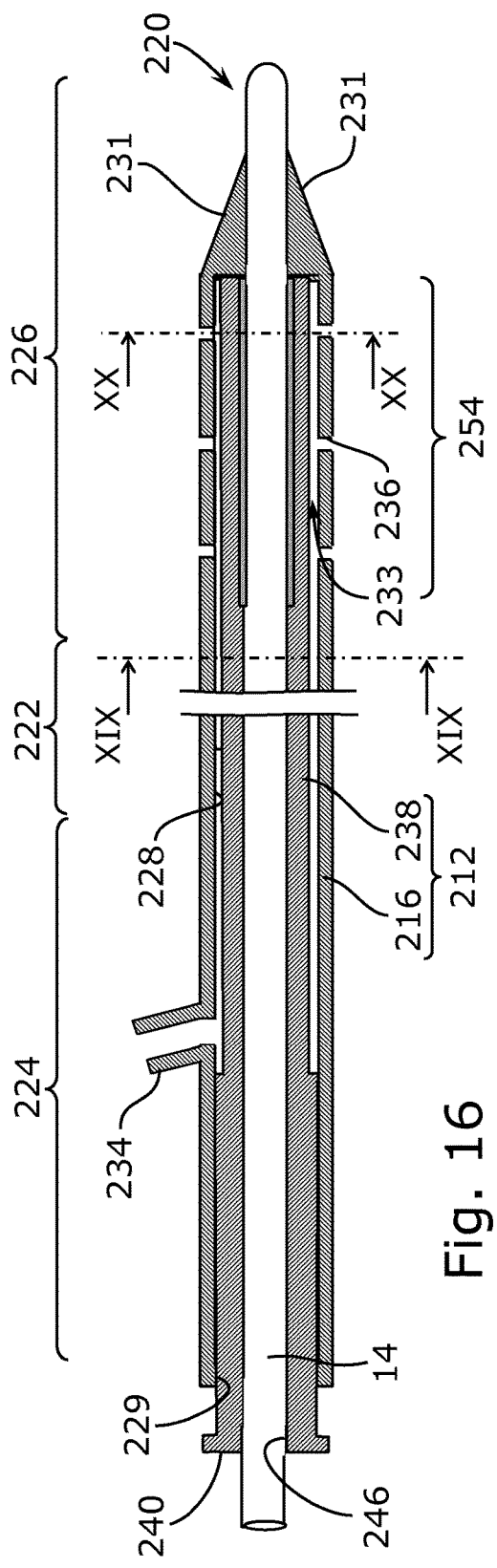
FIG. 16, a schematic axial cross-sectional view of the surgical device of FIG. 15, in rectilinear position, in section plane XVI-XVI of FIG. 19.

Once the inner tubular body 238 is inserted into the lumen 228 of the outer tubular body 216, the ribs 232 bear against the inner wall 228 of the outer tubular body 216, as shown in FIGS. 16, 19 and 20. The rigid distal portion 254 of the inner tubular body 238 constitutes a stiffening element housed in the longitudinal lumen 228 and capable of sliding in the longitudinal lumen 228 between the retracted position shown in FIG. 15 and the stiffening position shown in FIG. 16. In the stiffening position of FIG. 16, the stiffening element 254 is housed in the distal portion with shape memory 226 of the outer tubular body 216 and imposes a straightened configuration on the distal portion with shape memory 226. In the retracted position, on the other hand, the stiffening element 254 is housed outside the distal portion with shape memory 226 of the outer tubular body 216, allowing it to return to its curved rest position, as shown in FIG. 15. There are naturally an infinite number of positions between these two extreme positions: it is thus possible, by adjusting the relative position of the rigid distal portion 254 of the inner tubular body 238 and the distal portion with shape memory 226 of the outer tubular body 216, to continuously vary the orientation of the distal portion with shape memory 226 between its rest position and the straight position.

The proximal portion 250 and the intermediate portion 252 of the inner tubular body 238 constitute a link between the stiffening element 254 and the proximal end 240 of the inner tubular body 238, which always projects from the proximal end 218 of the outer tubular body 216. Communication channels 233 are intended to provide one or more pathways from the proximal connection 234 to the distal side ports 236, between the inner tubular body 238 and the outer tubular body 216, in particular for injecting a liquid, for example a contrast agent or a drug. The absence of ribs 232 in the proximal section 252.1 of the intermediate portion 252 of the inner tubular body 238 allows a good distribution of the liquid between the communication channels 233. The sealed interface between the inner tubular body 238 and the proximal port 229 and between the wire guide 14 and the distal port 230 also ensures that the liquid injected by the proximal connection 234 is ejected mainly through at least the distal side ports 236. The pathways are formed both when the inner tubular body 238 is in the stiffening position, as shown in FIG. 16, and when the inner tubular body 238 is retracted in the position shown in FIG. 15.

Figure 22:
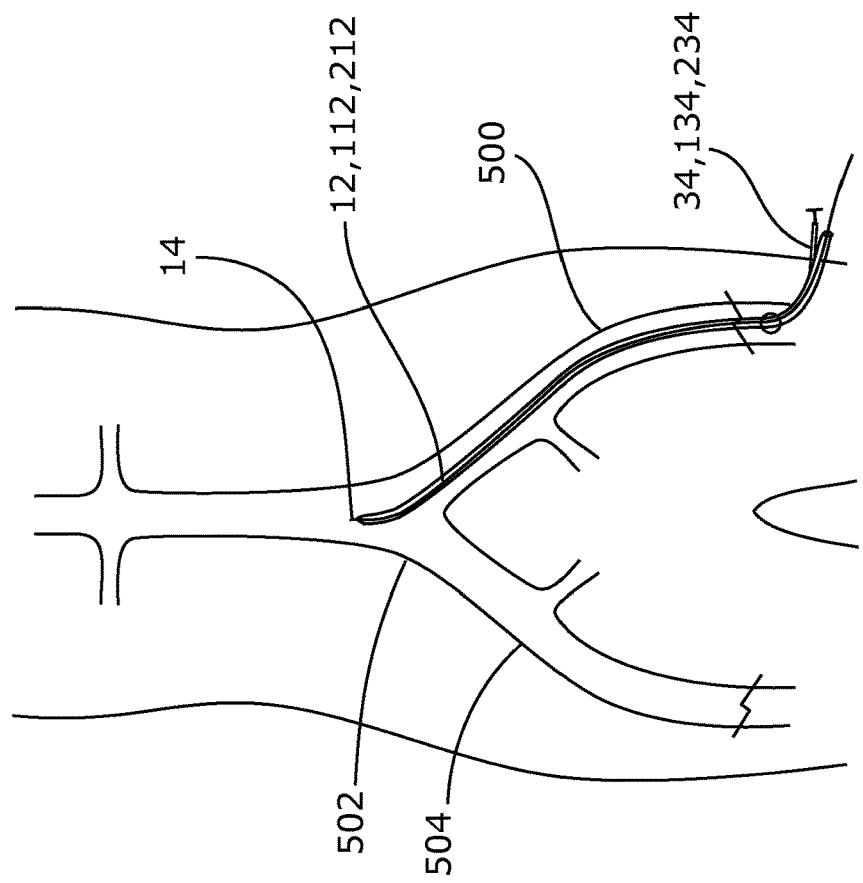
FIG. 22, a schematic view of a second step of a surgical operation using the surgical device according to the invention.
Figure 21:
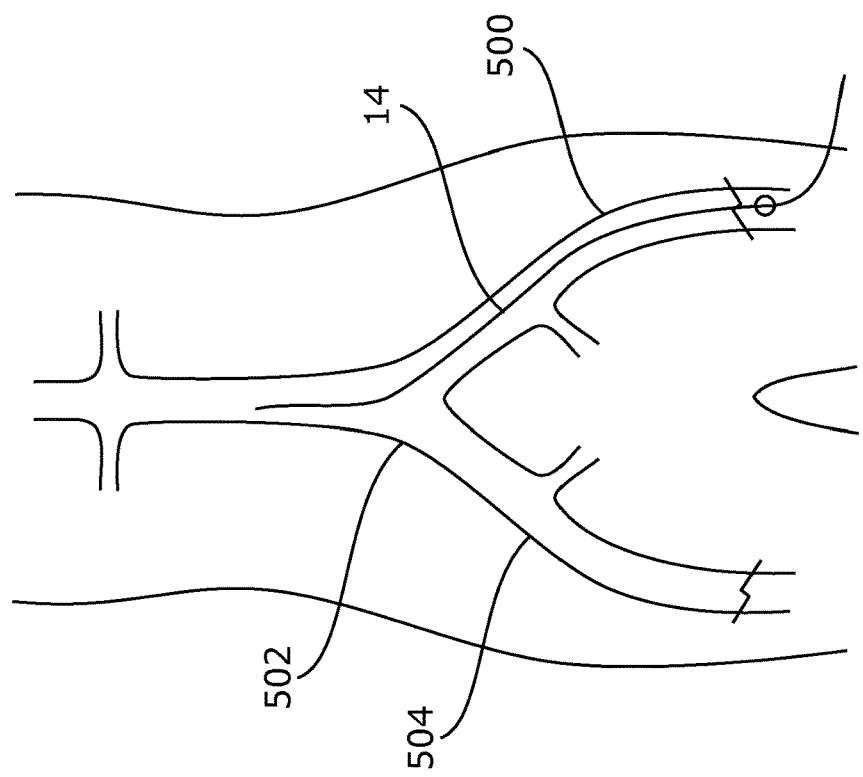
FIG. 21, a schematic view of a first step of a surgical operation using a surgical device according to the invention.
Figure 25:
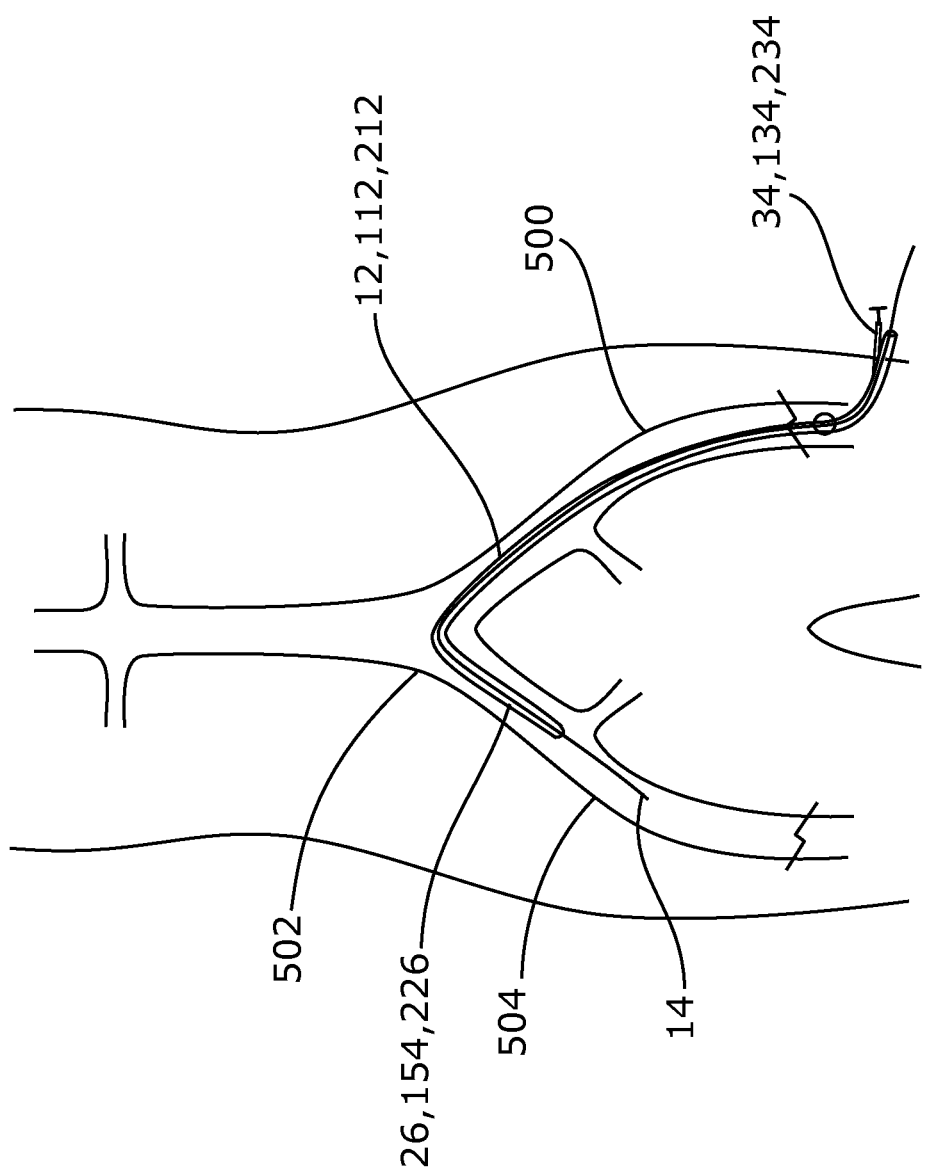
FIG. 25, a schematic view of a fifth step of a surgical operation using the surgical device according to the invention.

The surgical device 10, 110, 210 according to the various embodiments discussed can be used as follows, shown in FIGS. 21 to 25. First, the wire guide 14 is inserted into a first blood vessel 500—in the example shown in FIG. 21 the femoral artery—up to a junction 502 of a second blood vessel 504, here the common iliac artery. The orientable catheter 12, 112, 212 is inserted into the first blood vessel 500, as shown in FIG. 22, with the second tubular body 38, 138, 238 in the stiffening position, by causing the wire guide 14 to penetrate the longitudinal lumen 44, 128, 244 of the inner tubular body 38, 116, 238. If necessary, the wire guide 14 can be partially retracted so that its end coincides with the distal end of the inner tubular body 38, 116, 238, and the second tubular body 38, 138, 238 and the stiffening element 58, 158, 258 are retracted into the retracted position. The removal of the stiffening element 58, 158, 258 releases the distal portion with shape memory from the first tubular body, which expands and penetrates the junction of the second blood vessel as shown in FIG. 23. For visual monitoring of the operation, a contrast liquid can be injected through the proximal connection 34, 134, 234, the communication channels 33, 133, 233 and the distal side ports 36, 136, 236, at least in the retraction position of the second tubular body 38, 138, 238, and also in the stiffening position, for the embodiments allowing liquid distribution through the distal side ports 36, 136, 236 in this position. By playing on the position of the stiffening element 54, 154, 254 with respect to the distal portion with shape memory 26, 126, 226, the inflection of the distal portion 26, 126, 226 of the first tubular body 16, 116, 216 can be modified until the desired orientation is obtained. The wire guide 14 is then pushed back as shown in FIG. 24, so that the wire guide 14 opens at the distal end 20, 120, 220 of the first tubular body 16, 116, 216 and progresses into the second blood vessel 504. The second tubular body 38, 138, 238 can then be slid into the stiffening position by holding the wire guide 14 and the middle section 22, 122, 222 of the first tubular body 16, 116, 216 stationary. Finally, the orientable catheter 12, 112, 212 is slid onto the wire guide 14 to move the catheter 12, 112, 212 into the second blood vessel 504, as shown in FIG. 25.

Naturally, the examples shown in the figures and discussed above are given only by way of example and are not exhaustive. There is explicit provision for these various illustrated embodiments to be combined to propose other ones.

In particular, it is also possible to consider an embodiment in which the stiffening element is formed by the outer tubular body (as in the second embodiment) and is provided with longitudinal ribs that guide, delimit the longitudinal channels and stiffen the stiffening element (as in the third embodiment).

The guide ribs 133 can be omitted in the second embodiment. In this case, a clearance between the wire guide 14 and the cylindrical wall of the lumen 128 can be provided, in order to preserve a communication channel for the injection of a product in the presence of the wire guide 14. Alternatively, the wire guide 14 can be removed before the product is injected through the proximal port 129, in which case the proximal connection 134 can also be omitted.

Special coatings can be provided to facilitate sliding between the wire guide 14 and the lumen 44, 244 or the ribs 132, and the sealing of the end ports 129, 30, 130, 230. Sealing gaskets can also be provided for the end ports. Similarly, special coatings, or a careful choice of materials, can be provided to facilitate sliding between the first tubular body 16, 116, 216 and the second tubular body 38, 138, 238.

At least one of the tubular bodies can be expected to have an oval cross-section rather than a circular cross-section. In particular, it is foreseeable to the cylindrical inner tubular body with circular cross-section to slide into an outer tubular body with an oval-shaped inner lumen. Conversely, it is possible to provide for the inner tubular body with oval outer cross-section to slide into an outer tubular body whose lumen has a cylindrical cross-section. In both cases, the difference in the shape of the cross-sections makes it possible to define communication channels for the injection of a drug or a contrast agent, which makes it possible to do away with guide ribs, if necessary. More generally, the tubular bodies and their longitudinal lumens may be of any cross-section, provided that sufficient contact is made between the walls of the longitudinal lumen of the outer tubular body and the outer wall of the inner tubular body.

It is stressed that all the characteristics, as they emerge for a person skilled in the art from this description, the drawings and the attached claims, even if in practice they have only been described in relation to other specific characteristics, both individually and in any combinations, may be combined with other characteristics or groups of characteristics disclosed here, provided that this has not been expressly ruled out or that technical circumstances make such combinations impossible or meaningless.

The invention claimed is:

1. An orientable catheter comprising:
a first tubular body having a proximal end, a distal end, a longitudinal lumen opening through a proximal port onto the proximal end of the first tubular body and through a distal port onto the distal end of the first tubular body, a proximal portion including the proximal end of the first tubular body, a flexible median portion and a distal portion with shape memory having a curved configuration at rest, the distal portion with shape memory of the first tubular body being provided with one or more distal side ports opening into the longitudinal lumen of the first tubular body,
a second tubular body having a proximal end, a distal end, a longitudinal lumen opening through a proximal port onto the proximal end of the second tubular body and through a distal port onto the distal end of the second tubular body, a proximal portion including the proximal end of second first tubular body and a distal stiffening portion forming a stiffening element capable of sliding relative to the first tubular body between a stiffening position in which the stiffening element imposes a straightened configuration on the distal portion with shape memory, and a retracted position in which the stiffening element does not interfere with the resting curved configuration of the distal end with shape memory,
wherein the first tubular body is an outer tubular body, the second tubular body is an inner tubular body slidable inside the longitudinal lumen of the outer tubular body to slide the stiffening element between the stiffening position and the retracted position,
the longitudinal lumen of the inner tubular body has an inner diameter suitable for inserting and sliding a cylindrical wire guide with a circular base of a given diameter,
the distal port of the first tubular body is cylindrical and matches the cross-section of the wire guide, such that the wire guide can slide into the distal port of the first tubular body while sealing the distal port of the first tubular body, and the orientable catheter comprises one or more communication channels connecting the proximal portion of the first tubular body with the distal side ports when the stiffening element is in the retracted position and when the stiffening element is in the stiffening position.

2. The orientable catheter of claim 1, wherein the distal portion with shape memory of the first tubular body includes an end portion comprising a distal end of the first tubular body and having a cross-section that gradually increases from the distal end of the first tubular body away from the distal end of the first tubular body.

3. The orientable catheter of claim 1, wherein the outer tubular body has a cylindrical outer wall with a circular base.

4. The orientable catheter of claim 3, wherein the distal portion of the outer tubular body has an end portion comprising a distal end of the outer tubular body and having a cross-section that gradually increases from the distal end of the outer tubular body away from the distal end of the outer tubular body until the cylindrical outer wall.

5. The orientable catheter of claim 1, wherein the first tubular body has a flexible median portion, the distal portion with shape memory being located between the flexible median portion of the first tubular body and the distal end of the first tubular body.

6. The orientable catheter of claim 1, wherein the one or more communication channels together have an area of more than 0.15 mm$^2$ in cross-section when the stiffening element is in the retracted position.

7. The orientable catheter of claim 1, wherein the one or more communication channels are delimited at least partially by a wall of the longitudinal lumen of the first tubular body, at least when the stiffening element is in the retracted position.

8. The orientable catheter of claim 1, wherein the proximal portion of the first tubular body is provided with a lateral or axial access connection, communicating with the one or more communication channels.

9. A surgical device comprising the orientable catheter of claim 1 and a flexible wire guide capable of being inserted into the longitudinal lumen of the inner tubular body and exiting through the distal port of the first tubular body, wherein the distal port of the first tubular body is cylindrical and matches the cross-section of the wire guide, such that the wire guide is able to slide into the distal port of the first tubular body while sealing the distal port of the first tubular body.

10. An orientable catheter comprising:

a first tubular body having a proximal end, a distal end, a longitudinal lumen opening through a proximal port onto the proximal end of the first tubular body and through a distal port onto the distal end of the first tubular body, a proximal portion including the proximal end of the first tubular body, a flexible median portion and a distal portion with shape memory having a curved configuration at rest, the distal portion with shape memory of the first tubular body being provided with one or more distal side ports opening into the longitudinal lumen of the first tubular body, a second tubular body having a proximal end, a distal end, a longitudinal lumen opening through a proximal port onto the proximal end of the second tubular body and through a distal port onto the distal end of the second tubular body, a proximal portion including the proximal end of second first tubular body and a distal stiffening portion forming a stiffening element capable of sliding relative to the first tubular body between a stiffening position in which the stiffening element imposes a straightened configuration on the distal portion with shape memory, and a retracted position in which the stiffening element does not interfere with the resting curved configuration of the distal end with shape memory, wherein the second tubular body is an outer tubular body, the first tubular body is an inner tubular body slidable inside the longitudinal lumen of the outer tubular body to slide the stiffening element between the stiffening position and the retracted position, the orientable catheter comprises one or more communication channels formed at least partially in the longitudinal lumen of the inner tubular body and connecting the proximal portion of the first tubular body with the distal side ports at least when the stiffening element is in the retracted position, the distal side ports are covered by the stiffening element in the stiffening position, and the distal port at the distal end of the inner tubular body has longitudinal ribs suitable for allowing snug sliding of a wire guide, while preserving one or more distal ejection channels between the longitudinal lumen of the inner tubular body and the outside.

11. The orientable catheter of claim 10, wherein the distal portion with shape memory of the first tubular body includes an end portion comprising a distal end of the first tubular body and having a cross-section that gradually increases from the distal end of the first tubular body away from the distal end of the first tubular body.

12. The orientable catheter of claim 10, wherein the outer tubular body has a cylindrical outer wall with a circular base.

13. The orientable catheter of claim 12, wherein the distal portion of the outer tubular body has an end portion comprising a distal end of the outer tubular body and having a cross-section that gradually increases from the distal end of the outer tubular body away from the distal end of the outer tubular body until the cylindrical outer wall.

14. The orientable catheter of claim 10, wherein the first tubular body has a flexible median portion, the distal portion with shape memory being located between the flexible median portion of the first tubular body and the distal end of the first tubular body.

15. The orientable catheter of claim 10, wherein the one or more communication channels together have an area of more than 0.15 mm2 in cross-section when the stiffening element is in the retracted position.

16. The orientable catheter of claim 10, wherein the one or more communication channels are delimited at least partially by a wall of the longitudinal lumen of the first tubular body, at least when the stiffening element is in the retracted position.

17. The orientable catheter of claim 10, wherein the proximal portion of the first tubular body is provided with a lateral or axial access connection, communicating with the one or more communication channels.

* * * * *